United States Patent
Richelsoph et al.

(10) Patent No.: US 6,958,066 B2
(45) Date of Patent: *Oct. 25, 2005

(54) ROD TO ROD CONNECTOR

(75) Inventors: Marc Richelsoph, Bartlett, TN (US); John Usher, Brighton, TN (US)

(73) Assignee: Aesculap II, Inc., Center Valley, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/386,882

(22) Filed: Mar. 12, 2003

(65) Prior Publication Data

US 2003/0153917 A1  Aug. 14, 2003

Related U.S. Application Data

(63) Continuation of application No. 09/781,466, filed on Feb. 12, 2001, now Pat. No. 6,602,253.

(51) Int. Cl.$^7$ ............................................. A61B 17/58
(52) U.S. Cl. ....................................................... 606/61
(58) Field of Search ............................. 606/61, 70, 71, 606/69; 403/90, 87, 110

(56) References Cited

U.S. PATENT DOCUMENTS

| | | | | |
|---|---|---|---|---|
| 2,638,301 A | * | 5/1953 | Smith ..................... | 248/229.15 |
| 3,499,222 A | * | 3/1970 | Edelman et al. ............ | 433/174 |
| 4,641,636 A | * | 2/1987 | Cotrel ........................ | 606/61 |
| 4,773,402 A | * | 9/1988 | Asher et al. ................. | 606/61 |
| 4,957,495 A | * | 9/1990 | Kluger ....................... | 606/58 |
| 5,002,542 A | * | 3/1991 | Frigg ......................... | 606/61 |
| 5,005,562 A | * | 4/1991 | Cotrel ........................ | 606/61 |
| 5,024,213 A | * | 6/1991 | Asher et al. ................. | 606/61 |
| 5,030,220 A | * | 7/1991 | Howland ..................... | 606/61 |
| 5,102,412 A | * | 4/1992 | Rogozinski .................. | 606/61 |
| 5,129,900 A | * | 7/1992 | Asher et al. ................. | 606/61 |
| 5,133,716 A | * | 7/1992 | Plaza ......................... | 606/61 |
| 5,147,359 A | * | 9/1992 | Cozad et al. ................ | 606/61 |
| 5,147,360 A | * | 9/1992 | Dubousset .................. | 606/61 |
| 5,154,718 A | * | 10/1992 | Cozad et al. ................ | 606/61 |
| 5,275,600 A | * | 1/1994 | Allard et al. ................ | 606/61 |
| 5,312,405 A | * | 5/1994 | Korotko et al. .............. | 606/61 |
| 5,330,473 A | * | 7/1994 | Howland ..................... | 606/61 |
| 5,334,203 A | * | 8/1994 | Wagner ....................... | 606/61 |
| 5,368,594 A | * | 11/1994 | Martin et al. ................ | 606/61 |
| 5,403,316 A | * | 4/1995 | Ashman ...................... | 606/61 |
| 5,439,463 A | * | 8/1995 | Lin ............................ | 606/61 |
| 5,522,816 A | * | 6/1996 | Dinello et al. ............... | 606/61 |
| 5,601,552 A | * | 2/1997 | Cotrel ........................ | 606/61 |
| 5,624,442 A | * | 4/1997 | Mellinger et al. ............ | 606/61 |
| 5,630,816 A | * | 5/1997 | Kambin ....................... | 606/61 |
| 5,662,653 A | * | 9/1997 | Songer et al. ............... | 606/61 |
| 5,683,393 A | * | 11/1997 | Ralph ......................... | 606/61 |
| 5,928,232 A | * | 7/1999 | Howland et al. ............. | 606/61 |
| 5,947,966 A | * | 9/1999 | Drewry et al. ............... | 606/61 |
| 5,980,523 A | * | 11/1999 | Jackson ...................... | 606/61 |
| 6,063,089 A | * | 5/2000 | Errico et al. ................. | 606/61 |
| 6,110,173 A | * | 8/2000 | Thomas, Jr. .................. | 606/61 |
| 6,113,600 A | * | 9/2000 | Drummond et al. .......... | 606/61 |
| 6,171,311 B1 | * | 1/2001 | Richelsoph .................. | 606/61 |
| 6,283,967 B1 | * | 9/2001 | Troxell et al. ................ | 606/61 |
| 6,602,253 B2 | * | 8/2003 | Richelsoph et al. .......... | 606/61 |
| 2002/0007183 A1 | * | 1/2002 | Lee et al. .................... | 606/61 |

Primary Examiner—Eduardo C. Robert
(74) Attorney, Agent, or Firm—Kohn & Associates, PLLC

(57) ABSTRACT

A transverse connector having a seat rod for seating a rod therein engagement mechanism including a rod engagement seat forming a portion of the rod seat, the engagement mechanism being movable into and out of engagement with the rod seated in the rod seat.

1 Claim, 3 Drawing Sheets

ROD TO ROD CONNECTOR

This is a continuation application of U.S. Ser. No. 09/781,466, filed Feb. 12, 2001, now U.S. Pat. No. 6,602,253, which is incorporated herein by reference.

BACKGROUND OF THE INVENTION

1. Technical Field

The present invention generally relates to orthopedic devices. More specifically, the present invention is a surgical tool or medical construct used with spinal rods for the purpose of spinal fixation and correction of spinal curve.

2. Description of Related Art

Spinal rods are often used for spinal fixation, often times for correction of scoliotic curves. Fixation using such rods often involves implantation of rods and attaching them to the spine by hooks and/or screws. Usually, a pair of rods are placed on opposite sides of the portion of the spine to be fixed.

Various systems have been developed for cross linking spinal rods to prevent rod migration and to increase stiffness of the paired rod assembly.

Many assemblies used for interconnecting spinal rods, commonly referred to as transverse connector assemblies or rod to rod couplers, utilize a plate mechanism having openings therethrough for adjustably retaining hook systems that are bolted in place in the plate. Examples of such systems are in the U.S. Pat. No. 5,334,203 to Wagner, issued Aug. 2, 1994 and U.S. Pat. No. 5,522,816 to Dinello et al., issued Jun. 4, 1996. The U.S. Pat. No. 5,498,263 to Dinello et al., issued Mar. 12, 1996 discloses a transverse connector system utilizing set screws to interconnect vertebrae coupling members while also using plate members as described above for interconnecting the coupling members. A squared unit is formed having two sides defined by the plate members and two sides defined by the spaced rod members.

The U.S. Pat. No. 5,312,405 to Korotko et al., issued May 17, 1995 discloses a coupler used for interconnecting spinal rods wherein the coupler itself is a two piece unit. The neck portion of each unit is interconnected by a screw mechanism which clamps a male portion within a female portion of the system. The system also utilizes coupler inserts or yokes which engage a rod and are compressed about the rod when disposed within a seat portion of each coupler and compressed by an instrument which engages the bottom of the rod between the rod and the spine and the top of the coupler.

In further attempts to overcome these problems, various patents have disclosed devices wherein the set screw directly contacts the rod. Examples of such patents include U.S. Pat. No. 6,113,600 to Drummond et al, U.S. Pat. No. 5,624,442 to Mellinger et al, and U.S. Pat. No. 5,601,552 to Cotrel. In these patents, the force required to lock the set screw causes deformation of the rod at the point of contact of the set screw. This is more severe in cases where the set screw tip is conically shaped such as that found in FIG. 6 of the Drummond et al patent. This causes deeper, more localized deformation and therefore stress inducing indentation that can cause lower rod fatigue life. Additionally, the depth of the notch, as well as the induced localized stress is subject to random values based on how tight the surgeon tightens the set screw at the time of surgery.

Numerous spinal rod systems have also been developed which provide transverse connectors for linking the adjacent spinal rods across the spinal midline to provide a rigid and stable construct. Most of these systems present one or more difficulties for spinal surgeons. Many of the devices are high profile which increases soft tissue trauma and surgical complications. Furthermore, in many of these prior art systems, the attachment devices must be preloaded on the spinal rods which can require significant pre-operative planning and which virtually eliminates the opportunity to add connectors in situ.

One transverse connector system is the TSRH® CROSSLINK® of Danek Medical, Inc. The TSRH® CROSSLINK® utilizes a three point shear clamp mechanism which restricts motion between the rods in all directions, and particularly resists axial forces between rods and torsional moments about the axis of the rods. A quadrilateral construct is formed by laterally connecting the rods across the sagittal plane with rigid plates. The lateral connection reduces the loss of correction that can occur over time.

Rigid transverse connections between spinal rods are beneficial because they restrict rod migration and increase construct stiffness. In many cases involving multi-level fusion of the spine, these features are essential while solid bone fusion is accomplished. In the post-operative period before fusion occurs, a significant amount of motion can occur between the rods, wires and hooks, which can, for example, allow a scoliotic correlation to decrease or the pelvis to de-rotate toward its previous, deformed position. By providing a rigid transverse connection between two spinal rods, the loss of correction can be reduced and a stiffer construct can be created which may enhance the promotion of a solid fusion. While the TSRH® CROSSLINK® provides an excellent construct, a need has remained for low profile devices where the surface area of contact with the rod is greatly increased and thus minimizes localized stress regardless of how tight the set screw is set.

It is desirable to provide a coupler which engages a rod by a simple locking mechanism. It is also desirable to provide a simple interconnecting mechanism between couplers which requires few parts and little manipulation to provide the interconnection. Further, it is desirable to provide a transverse coupler assembly which requires only a simple screw driver or nut driver outside of the assembly for its interconnection between a pair of spinal rods. It is also useful to develop a mechanism having a surface area of contact with the rod that is greatly increased and thus minimizes localized stress regardless of how tight the set screw is set.

SUMMARY OF THE INVENTION

According to the present invention, there is provided a transverse connector having a rod seat for seating a rod therein and an engagement mechanism including a rod engagement seat forming a portion of the rod seat, the engagement mechanism being movable into and out of engagement with the rod seated in the rod seat.

DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1A:
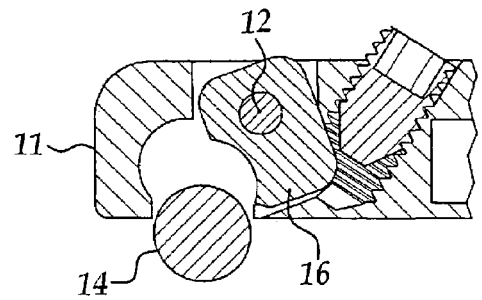
FIGS. 1A–C are side views, partially in cross section of a rod to rod coupler made in accordance with the present invention.

The present invention provides a transverse connector generally indicated at 10 including a rod seat 12 for seating a rod 14 therein, an engagement mechanism 16 including a rod engagement seat forming a portion of the rod seat 12 wherein the engagement mechanism 16 is movable into and out of engagement with the rod 14 seated in the rod seat 12.

By "engagement mechanism 44" as used herein, it is meant any item which can be used to hold a rod 14 in proper position within the rod seat 12. This engagement mechanism 44 can include, but is not limited to, a locking tab 16, and other similarly shaped devices which can provide sufficient surface area contact with the rod 14. Critically, unlike other point contact devices, the present invention provides a surface to surface contact. Accordingly, deformation of the rod is minimized or eliminated.

In accordance with the present invention, a connector 10 is provided which includes an engagement mechanism 44 to rigidly hold spinal components, such as two longitudinal rods 14, apart at various distances. A connector body 11, which is provided in multiple lengths in both fixed and adjustable configurations, includes a seat portion 12 for sections of each rod 14. An engagement mechanism 44 is provided within the connector body 10 for each rod 14. The engagement mechanism 44 includes a partial rod seat 12. A portion of the engagement mechanism 44, sufficient to allow the connector body 11 to be pushed on the rod 14, is free to move within the connector body 11. Thus the engagement mechanism 44 does not interfere with the placement of the connector body 11 over the rods 14. When properly placed and sized, at least one actuating mechanism 48 is tightened to secure the assembly 10. This forces the engagement mechanism 44 outward relative to the actuating mechanism 48 and against the rods 14 while each of the rods 14 are forced against the seat portion 12 in the connector body 11.

The engagement mechanism 44 is held in place using an affixing mechanism 20. This affixing mechanism 20 prevents undesired movement of the engagement mechanism 44. The affixing mechanism 20 can be a pivot, a screw or other similar affixing devices known to those of skill in the art.

The single actuating mechanism 48' embodiment is provided for simple locking of close rod constructs. The actuating mechanism 48' for this embodiment consists of, but is not limited to, a set screw 18' having a conical floating tip 32 or other tips known to those of skill in the art. This floating tip 32 compensates for manufacturing tolerances and provides equal force against each engagement mechanism 44' as the set screw 18' is advanced. This prevents localized stress, thereby preventing deformation of the rod 14'.

In one embodiment of the presents invention, there is provided an adjustable portion 34 which can consist of a male 38 and female 36 portion. The male 38 portion includes a groove 42 and the said female portion 38 includes a set screw 18 with an angled or rounded tip. The set screw 18, upon tightening, enters the groove 42 and securely holds the assembly 10 fixed at the desired length. The groove 42 provides increased surface area for the set screw 18 to hold against.

More, specifically, the transverse connector 10 of the present invention includes an actuating mechanism 48 for moving the rod engagement seat 46 into and out of engagement with rod 14 seated in the rod set 12. The actuating mechanism 48 includes any mechanism wihich forcibly moves the rod engagement seat 46 into and out of egagement with the rod 14 while maintaining the rod engagement seat 46 in the proper position. This actuating mechanism 48 can include, for example, multiple locking positions to keep the rod engagement seat 46 in a particular position. Alternatively, the engagement mechanism 46 can include a screw 18 which can be set to a specific tension based on the rod 14 being included therein and the specific tension required for the patient.

Additionally, the transverse connector 10 of the present invention can include a body portion 11 including at least one rod seat 12. The engagement mechanism 44 includes an insert/locking tab 16 which is movably connected to the body portion 11. In the preferred embodiment, the insert 16 is pivotally connected to the body portion 11 using an affixing mechanism 20. For example, the insert/locking tab 16 can be connected in any movable fashion known to those of skill in the art. For example, a screw, pivot pin, or other pivotable mechanism can be utilized.

The insert/locking tab 16 also includes a substantially arcuate recess 22 located in the corner of the insert/locking tab 16. The recess 22 defines the rod engagement seat 46 which is adjacent to the rod seat 12 of the body portion 11.

Also included on the insert/locking tab 16 is an abutment portion 24. The abutment portion 24 is located on the surface of the insert 16 and is located opposite the arcuate recess 22. The actuating mechanism 48 selectively engages the abutment portion 24 to selectively force the arcuate recess 22 towards the rod seat 22 thereby sandwiching the rod 14 therebetween.

In the preferred embodiment, the actuating mechanism 48 includes a set screw 18 threadedly engaged in the body portion 11. The set screw 18 is selectively movable towards and away from the engagement with the abutment portion 24.

Figure 1B:
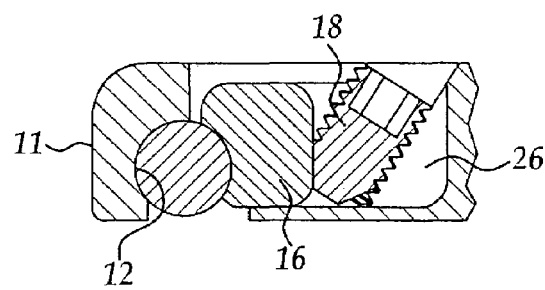

An alternative embodiment of the present invention is shown in FIG. 1B. The insert/locking tab 16 is disposed in a recess 26 within the body portion 11. The insert/locking tab 16 Is slideable within the recess 26.

Figure 5:
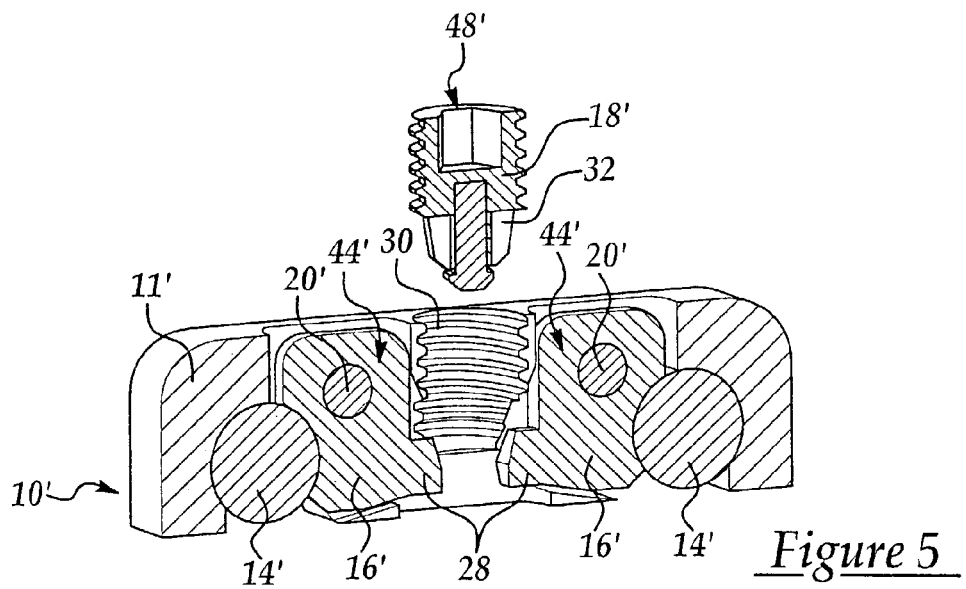
FIG. 5 is a side view, partially in cross section of another embodiment of the rod to rod coupler of the present invention.
Figure 6:
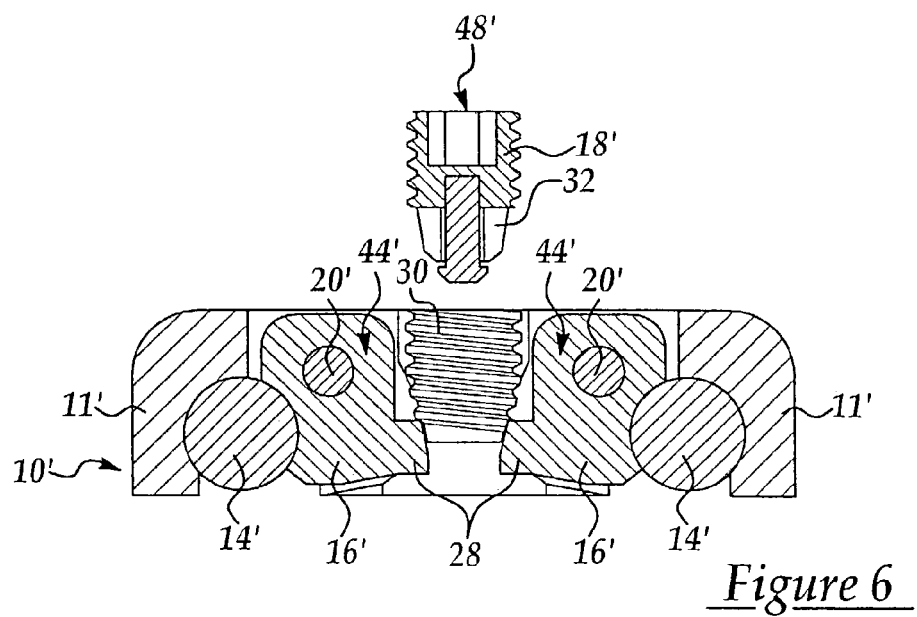
FIG. 6 is a cross sectional side view of an embodiment of the rod to rod coupler of the present invention.
Figure 7:
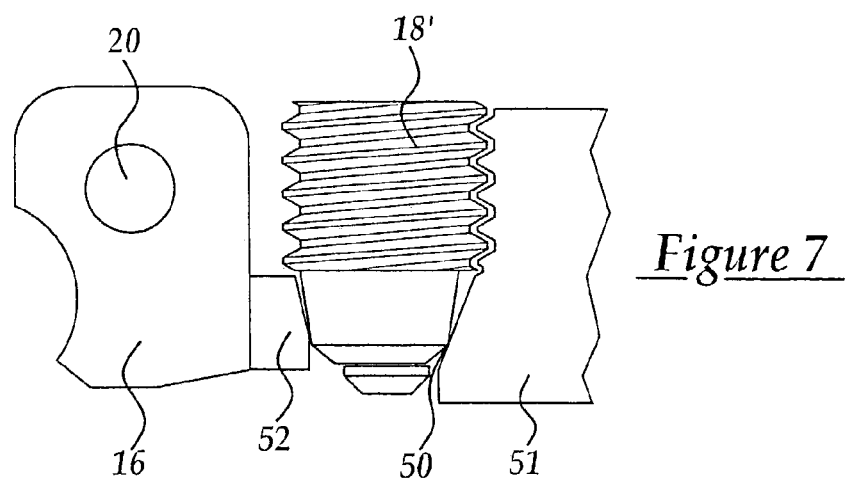
FIG. 7 is a side view of the set screw according to the present invention.

Also provided by the present invention is a transverse connector 10 as shown in FIGS. 5 and 6, including a pair of oppositely opposed insert/locking tabs 16'. The inserts/locking tab 16' are adjacent to spaced rod seats 12' of the body portion 11'. Each of the abutment portions 24' of the inserts/locking tabs 16' include a shoulder portion 28 extending towards each other, as shown in FIGS. 5 and 6.

The actuating mechanism 18' simultaneously engages each shoulder 28 portion. The single actuating mechanism 48' moves each of the inserts 16' into engagement with the rod 14' and each of the rod seats 12'.

Additionally, the body portion 11' of the transverse connector 10' can include a threaded opening 30 whereby the shoulder portions 28 extend into the opening 30 such that when the actuating mechanism 48', including a set screw 18', is threadedly engaged in the opening 30, the actuating mechanism 48 can simultaneously engage both shoulder portions 28. This movement actuates movement of the inset/locking tab 16' into engagement with the rod 14' seated in the rod seat 12'. Alternatively, the set screw 18' can be placed into engagement using any locking mechanism or manually being pushed into the opening 30.

Figure 1C:
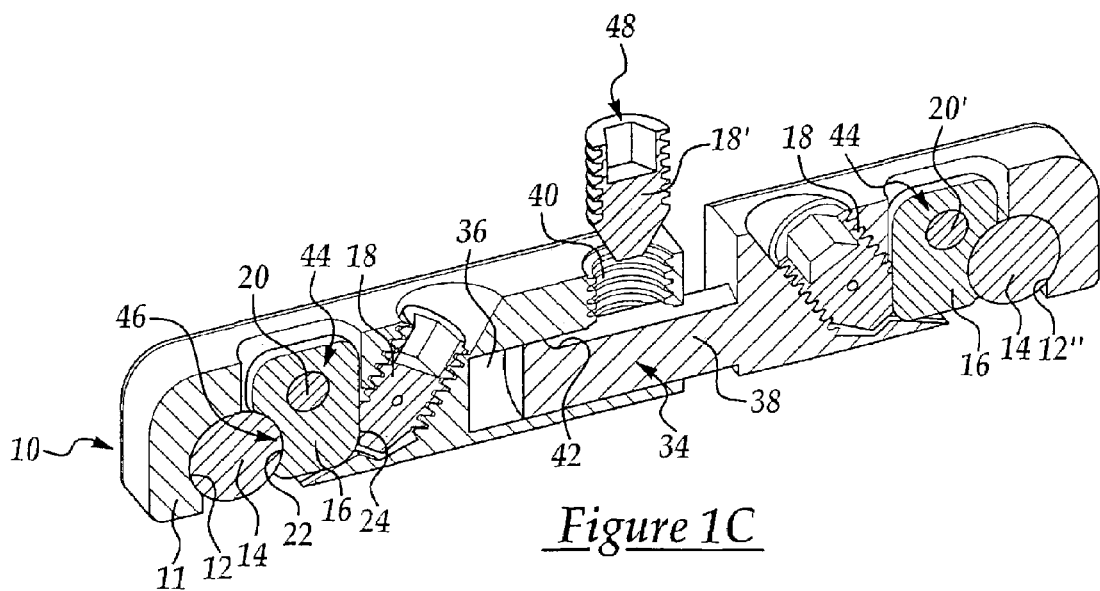

In FIG. 1 the transverse connector 10 of the present invention also provides a set screw 18' which can include a floating tip 32 for evenly applying the load to both of the shoulder portions 28 simultaneously. The floating tip 32 self adjusts to evenly apply the load to both insert/locking tab 16' simultaneously. This tip 32 prevents the set screw 18' from applying more pressure to one insert/locking tab 16' versus the other insert/locking tab 16'.

Figure 2:
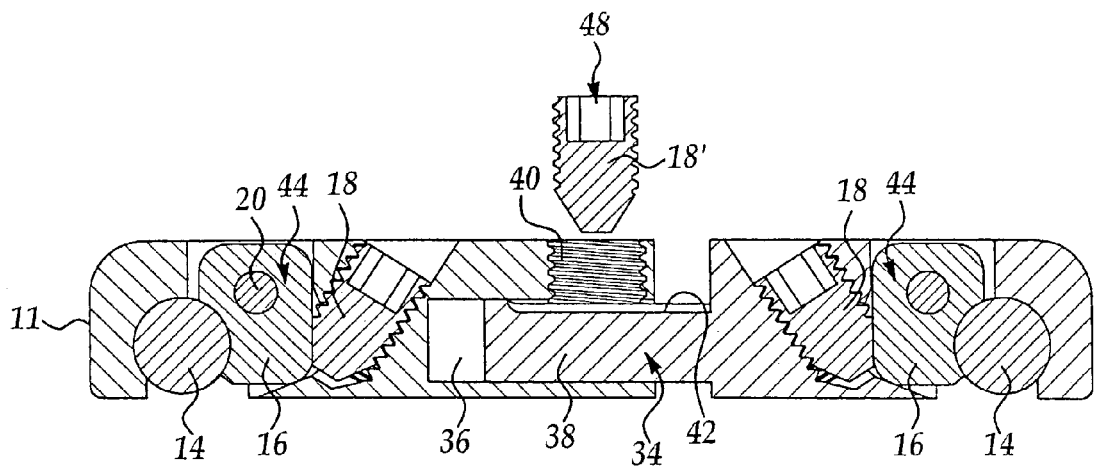
FIG. 2 is a cross sectional side view of a rod to rod coupler made in accordance with the present invention.
Figure 3:
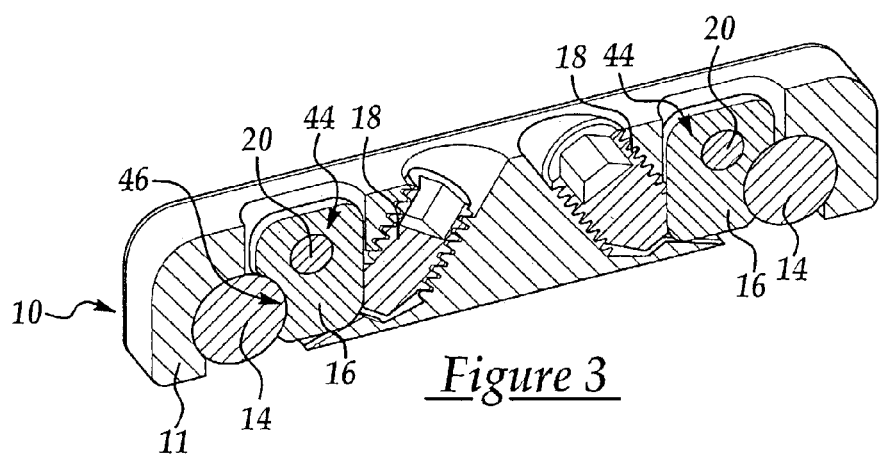
FIG. 3 is a side view, partially in cross section of a second embodiment of the rod to rod coupler made in accordance with the present invention.
Figure 4:
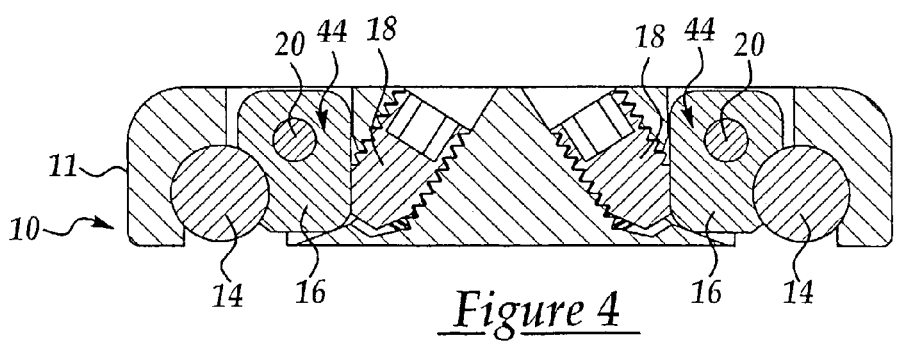
FIG. 4 is a cross sectional side view of a rod to rod coupler made in accordance with the present invention.

In a further embodiment, as shown in FIGS. 1 and 2, the transverse connector 10 of the present invention provides a body portion 11 having at least a pair of rod seats 12. In this embodiment, the body portion 11 can include a length adjustment mechanism 34 for adjusting the distance between the pair of rod seats 12. In the preferred embodiment, the body portion 11 includes a first portion including one of the rod seats 12 having a female opening 36 and a second portion including a second rod seat 12 and a male portion 38 which is slideably seated in the female opening 36. Also provided is a length locking mechanism 40 for locking the male portion 38 at a fixed position relative to the female portion 36 thereby establishing a distance between the rod seats 12 and 12'. The practitioner, when inserting the mechanism, obtains precise distance adjustments between rod seats 12.

The male portion 38 can also include a groove 42 along the length of the male portion 38. In this embodiment, the locking mechanism 40 includes a set screw 18' for selective engagement with the groove 42.

Also provided by the present invention is a set screw which applies load against an implant 51. The set screw 18' can have a conical floating tip 32 or other tips known to those of skill in the art.

The set screw 18' distributes load between the two implant engagement mechanism 50, 52 in which the set screw 18' is placed. The set screw 18' can therefore shift and distribute load between the two mechanisms 50, 52 while securely locking an additional implant component in place.

In one embodiment of the present invention, the implant engagement mechanisms 50, 52 are both movable. Alternatively, one mechanism 50 can be movable while the other mechanism 52 is fixed and therefore does not allow any movement.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

REFERENCES

U.S. Pat. No. 2,638,301, Smith et al.
U.S. Pat. No. 3,499,222, Linkow et al.
U.S. Pat. No. 4,641,636, Cotrel et al.
U.S. Pat. No. 4,773,402, Asher et al.
U.S. Pat. No. 4,957,495, Kluger et al.
U.S. Pat. No. 5,002,542, Frigg et al.
U.S. Pat. No. 5,005,562, Cotrel et al.
U.S. Pat. No. 5,024,213, Asher et al.
U.S. Pat. No. 5,030,220, Howland et al.
U.S. Pat. No. 5,102,412, Rogozinski et al.
U.S. Pat. No. 5,129,900, Asher et al.
U.S. Pat. No. 5,133,716, Plaza et al.
U.S. Pat. No. 5,147,359, Cozad et al.
U.S. Pat. No. 5,147,360, Debousset et al
U.S. Pat. No. 5,154,718, Cozad et al.
U.S. Pat. No. 5,275,600, Allard et al:
U.S. Pat. No. 5,312,405, Korotko et al.
U.S. Pat. No. 5,330,473, Howland et al.
U.S. Pat. No. 5,334,203, Wagner et al.
U.S. Pat. No. 5,368,594, Martin et al.
U.S. Pat. No. 5,403,316, Ashman et al.
U.S. Pat. No. 5,439,463, Lin et al.
U.S. Pat. No. 5,522,816, Dinello et al.
U.S. Pat. No. 5,601,552, Cotrel et al.
U.S. Pat. No. 5,624,442, Mellinger et al.
U.S. Pat. No. 5,630,816, Kambin et al.
U.S. Pat. No. 6,113,600, Drummond et al.

What is claimed is:

1. A transverse connector for engaging at least one rod comprising:
   a rod seat for seating a rod therein;
   engagement means including a rod engagement seat forming a portion of said rod seat, said engagement means including an insert pivotally fixed to said connector capable of rotating into and out of engagement with a rod seated in said rod seat and said insert including a substantially arcuate recess in one corner thereof for engaging a portion of the rod and defining a second portion of said rod seat; and
   screw means for screwingly engaging said insert into engagement with the rod seated in said rod seat.

* * * * *